United States Patent
Cho

(10) Patent No.: US 11,904,142 B2
(45) Date of Patent: Feb. 20, 2024

(54) NEEDLELESS INJECTION SYRINGE

(71) Applicant: Min Su Cho, Incheon (KR)

(72) Inventor: Min Su Cho, Incheon (KR)

( * ) Notice: Subject to any disclaimer, the term of this patent is extended or adjusted under 35 U.S.C. 154(b) by 917 days.

(21) Appl. No.: 16/904,873

(22) Filed: Jun. 18, 2020

(65) Prior Publication Data

US 2020/0316302 A1      Oct. 8, 2020

Related U.S. Application Data

(63) Continuation of application No. PCT/KR2018/015674, filed on Dec. 11, 2018.

(30) Foreign Application Priority Data

Dec. 19, 2017   (KR) .................. 10-2017-0174701
Dec. 10, 2018   (KR) .................. 10-2018-0157787

(51) Int. Cl.
  *A61M 5/30*    (2006.01)
  *A61M 5/20*    (2006.01)
  *A61M 5/315*   (2006.01)

(52) U.S. Cl.
  CPC ............ *A61M 5/30* (2013.01); *A61M 5/2033* (2013.01); *A61M 5/31586* (2013.01); *A61M 2005/202* (2013.01); *A61M 2005/2073* (2013.01)

(58) Field of Classification Search
  None
  See application file for complete search history.

(56) References Cited

U.S. PATENT DOCUMENTS

| | | | |
|---|---|---|---|
| 5,569,189 | A | 10/1996 | Parsons |
| 5,599,302 | A | 2/1997 | Lilley et al. |
| 5,782,802 | A | 7/1998 | Landau |
| 2011/0319860 | A1 | 12/2011 | Williamson et al. |

FOREIGN PATENT DOCUMENTS

| | | |
|---|---|---|
| JP | 3255098 B2 | 2/2002 |
| KR | 1020010074767 A | 8/2001 |
| KR | 1020040074877 A | 8/2004 |
| KR | 100547166 B1 | 1/2006 |
| KR | 1020100023484 A | 3/2010 |
| KR | 101000589 B1 | 12/2010 |
| KR | 101743475 B1 | 6/2017 |

OTHER PUBLICATIONS

International Search Report of PCT/KR2018/015674 dated May 9, 2019.

*Primary Examiner* — Manuel A Mendez
(74) *Attorney, Agent, or Firm* — Dinsmore & Shohl LLP; Yongsok Choi, Esq.

(57) ABSTRACT

A needleless injector is provided. The needleless injector includes a loading lever having a working arm part having a lever shaft, a towing member inserted inside the cylinder housing, a link having one end portion pin-coupled to the working arm part and the other end portion pin-coupled to the towing member, an inner cylinder inserted inside the cylinder housing, a spring inserted into the inner cylinder, an actuating head inserted into the inner cylinder in front of the spring and having a catching protrusion configured to be inserted into the slit, and a trigger means having a stopper head part configured to be able to be inserted into the slit of the inner cylinder and detached from the slit. Accordingly, the needleless injector can achieve a reduction in size and thickness by having a simple structure even with a lever for reloading integrally formed therein.

10 Claims, 9 Drawing Sheets

NEEDLELESS INJECTION SYRINGE

CROSS-REFERENCE TO RELATED APPLICATION

This application is a continuation of International Application No. PCT/KR2018/015674 filed on Dec. 11, 2018 which claims priority to Korean Patent Application No. 10-2017-0174701 filed on Dec. 19, 2017 and Korean Patent Application No. 10-2018-0157787 filed on Dec. 10, 2018, the disclosure of which is incorporated herein by reference in its entirety.

BACKGROUND

1. Field of the Invention

The present invention relates to a needleless injector, and more particularly, to a needleless injector capable of achieving a reduction in size and thickness by having a simple structure even with a lever for reloading integrally formed therein.

2. Discussion of Related Art

Inventions relating to conventional needleless injectors have been disclosed in U.S. Pat. Nos. 5,599,302 and 5,782,802, Korean Patent Publication Nos. 10-2004-0074877 and 10-2001-0074767, and Japanese Patent No. 3255098, all of which adopt a method in which a piston rod, which is retracted with the compression of a spring, is loaded by engagement between a ball and a holder and, by switching to disengage the holder from the ball, the piston rod is triggered to be pushed forward by a force of the spring.

However, the above-described method using the locking and unlocking mechanism of the ball and the holder has problems in that the structure is relatively complex, a large number of parts and high precision are required, and a frequency of malfunction or failure due to wear and tear of parts by accumulated use is high.

Meanwhile, an invention that does not adopt the locking and unlocking mechanism of the ball and the holder has been disclosed in U.S. Pat. No. 5,704,911, but, regarding this invention, the fact that a separate link mechanism should be provided to reload a needleless injector that has been triggered one time may be pointed out as a drawback.

Such a link mechanism for reloading has also been disclosed in Korean Patent Registration No. 10-1000589 even though the invention adopts the locking and unlocking mechanism of the ball and the holder. The link mechanism disclosed in the invention is greatly improved in terms of portability in that the size is further reduced as compared to the above U.S. patent, but there is still room for improvement because the link mechanism is still provided separately from a needleless injector.

SUMMARY OF THE INVENTION

The present invention is directed to providing a needleless injector capable of achieving a reduction in size and thickness by having a simple structure even with a lever for reloading integrally formed therein.

To achieve the above-described objective, the present invention provides a needleless injector including: a cylinder housing; a loading lever having a working arm part having a lever shaft, which is rotatably coupled to a rear end portion of the cylinder housing, formed at one end portion and a handle part extending from the other end portion of the working arm part by being bent at a predetermined angle so that the handle part is rotatable to a folded position where the handle part lies on the cylinder housing; a towing member inserted inside the cylinder housing; a link having one end portion spaced apart from the lever shaft and pin-coupled to the working arm part and the other end portion pin-coupled to the towing member so that the towing member is able to slide back and forth inside the cylinder housing according to the rotation of the loading lever; an inner cylinder inserted inside the cylinder housing so as to be able to slide back and forth and having a rear end portion integrally coupled to the towing member, a front end portion configured to be closed by a stopper having a passage formed therein, and a slit extending rearward from the front end portion; a spring inserted inside the inner cylinder; an actuating head inserted inside the inner cylinder so as to be able to slide back and forth in front of the spring and having a catching protrusion configured to be inserted into the slit; and a trigger means coupled to an outer side of the cylinder housing and having a stopper head part configured to pass through the cylinder housing so as to be able to be inserted into the slit of the inner cylinder and detached from the slit.

The cylinder housing may have a cut section extending forward from the rear end portion to which the lever shaft is coupled. Movements of the working arm part and the link according to the rotation of the loading lever may occur through the cut section. At the folded position of the handle part, the working arm part may be at least partially accommodated in the cylinder housing through the cut section, and the link may be completely accommodated in the cylinder housing through the cut section.

The trigger means may include a trigger lever having the stopper head part formed at one side and a pressing part, which is configured to detach the stopper head part from the slit, formed at the other side with respect to a hinge shaft rotatably coupled to the outer side of the cylinder housing.

The needleless injector may further include a plug having a cylindrical part, whose outer circumferential surface is screw-coupled to an inner circumferential surface of a front end portion of the cylinder housing and whose inner circumferential surface forms a seating space, and a blocking plate part extending radially inward from a rear end portion of the cylindrical part and having a through-hole formed at a central portion.

To achieve the above-described objective, the present invention provides a needleless injector including: a cylinder housing; a loading lever having a working arm part having a lever shaft, which is rotatably coupled to a rear end portion of the cylinder housing, formed at one end portion and a handle part extending from the other end portion of the working arm part by being bent at a predetermined angle so that the handle part is rotatable to a folded position where the handle part lies on the cylinder housing; a towing member inserted inside the cylinder housing; a link having one end portion spaced apart from the lever shaft and pin-coupled to the working arm part and the other end portion pin-coupled to the towing member so that the towing member is able to slide back and forth inside the cylinder housing according to the rotation of the loading lever; a spring inserted inside the cylinder housing and whose rear end portion is coupled to the towing member; an actuating head inserted inside the cylinder housing, coupled to a front end portion of the spring, and having a catching protrusion configured to protrude radially toward an inner circumferential surface of the cylinder housing; and a trigger means coupled to an outer side of the cylinder housing and having a stopper head part configured to pass through the cylinder housing so as to be able to protrude and be detached from the inside of the cylinder housing.

The cylinder housing may have a cut section extending forward from the rear end portion to which the lever shaft is coupled. Movements of the working arm part and the link according to the rotation of the loading lever may occur through the cut section. At the folded position of the handle part, the working arm part may be at least partially accommodated in the cylinder housing through the cut section, and the link may be completely accommodated in the cylinder housing through the cut section.

The trigger means may include a trigger lever having the stopper head part formed at one side and a pressing part, which is configured to detach the stopper head part from the inside of the cylinder housing, formed at the other side with respect to a hinge shaft rotatably coupled to the outer side of the cylinder housing.

The needleless injector may further include a plug screw-coupled to a front end portion of the cylinder housing and having, from a rear end portion thereof, a blocking wall part, which has an accommodating groove formed to accommodate the actuating head, a passage part, which has a through-hole communicating with the accommodating groove formed to extend at a central portion, and a cylindrical part, which has an inner circumferential surface on which an inner seating space communicating with the through-hole is formed, sequentially formed in this order.

To achieve the above-described objective, the present invention provides a needleless injector including: a cylinder housing having a stopper wall formed at a rear end portion and a slit extending rearward from a front end portion; a loading lever having a working arm part having a lever shaft, which is rotatably coupled to the cylinder housing behind the stopper wall, formed at one end portion and a handle part extending from the other end portion of the working arm part by being bent at a predetermined angle so that the handle part is rotatable to a folded position where the handle part lies on the cylinder housing; a spring inserted inside the cylinder housing; an actuating head inserted inside an inner cylinder so as to be able to slide back and forth in front of the spring and having a catching protrusion, which is configured to protrude radially toward an inner circumferential surface of the cylinder housing, and a loading protrusion, which is configured to pass through the slit; a loading cylinder configured to be coupled to an outer side of the cylinder housing so as to be able to slide back and forth, configured to be coupled to the loading protrusion of the actuating head through an inner circumferential surface, and having an open section extending in a front-rear, longitudinal direction; a link having one end portion pin-coupled to the handle part at a position adjacent to the lever shaft and the other end portion pin-coupled to a rear end portion of the loading cylinder so that the loading cylinder is able to slide back and forth at the outer side of the cylinder housing according to the rotation of the loading lever; and a trigger means coupled to the outer side of the cylinder housing through the open section of the loading cylinder and having a stopper head part configured to pass through the cylinder housing so as to be able to protrude and be detached from the inside of the cylinder housing.

The cylinder housing may include a hinge plug coupled to a rear end portion of the cylinder housing and having a shaft accommodating part, to which the lever shaft is coupled, and the stopper wall.

The working arm part and the handle part of the loading lever may be perpendicular to each other.

The trigger means may include a trigger lever having the stopper head part formed at one side and a pressing part, which is configured to detach the stopper head part from the inside of the cylinder housing, formed at the other side with respect to a hinge shaft rotatably coupled to the outer side of the cylinder housing.

The needleless injector may further include a plug screw-coupled to a front end portion of the cylinder housing and having, from a rear end portion thereof, a blocking wall part, which has an accommodating groove formed to accommodate the actuating head, a passage part, which has a through-hole communicating with the accommodating groove formed to extend at a central portion, and a cylindrical part, which has an inner circumferential surface on which an inner seating space communicating with the through-hole is formed, sequentially formed in this order.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

Figure 1:
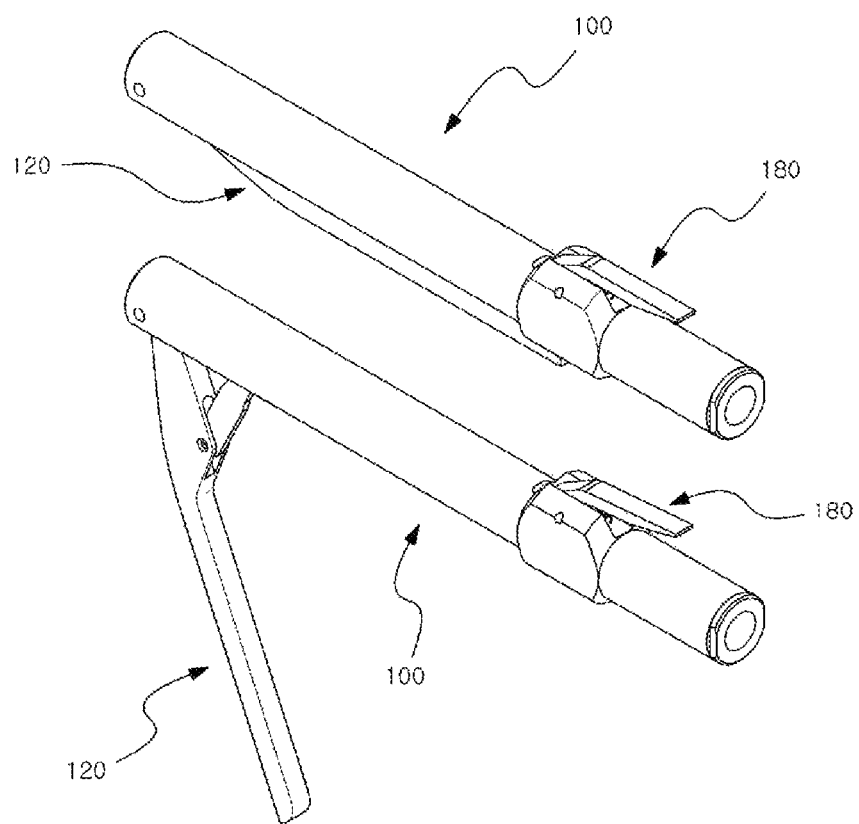
FIG. 1 is a perspective view illustrating states before and after the operation of a needleless injector according to a first embodiment of the present invention.

As illustrated in FIG. 1, a needleless injector 100 according to a first embodiment of the present invention includes a cylinder housing 110, a loading lever 120 rotatably coupled to a rear end portion of the cylinder housing 110, and a trigger lever 180 coupled to an outer side of the cylinder housing 110.

Figure 2A:
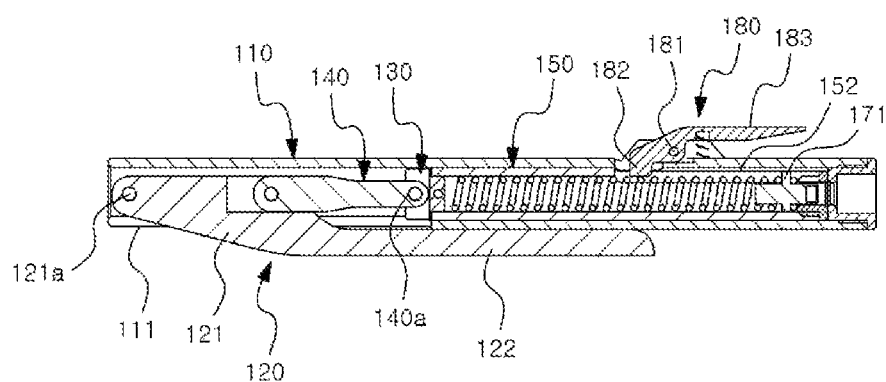
FIG. 2A is a cross-sectional view of the state before the operation of the needleless injector of FIG. 1.
Figure 2B:
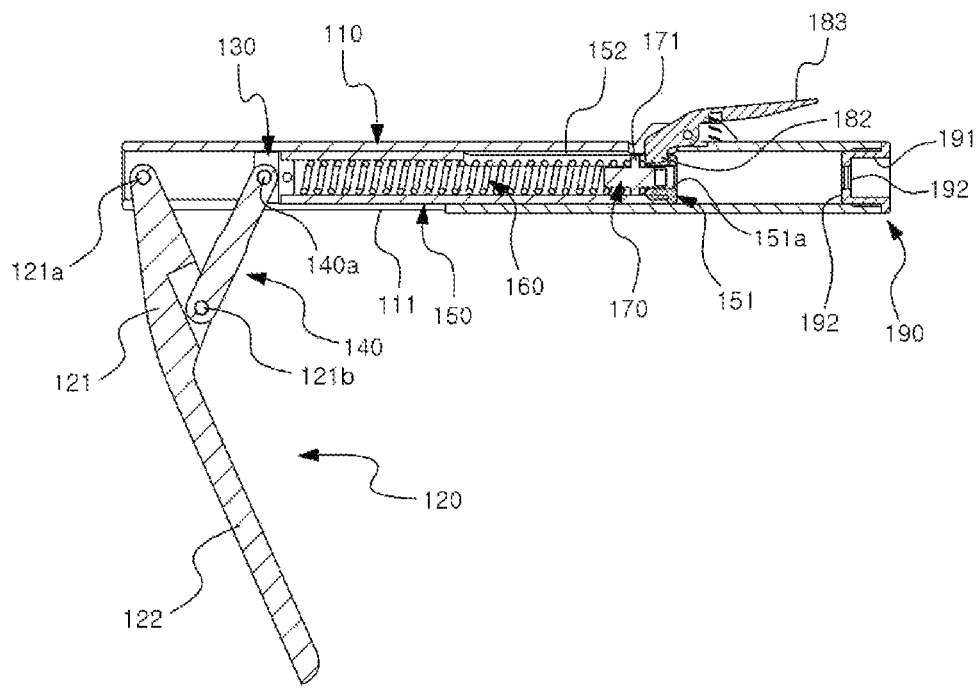
FIG. 2B is a cross-sectional view of the state after the operation of the needleless injector of FIG. 1.

As illustrated in FIG. 2, the loading lever 120 has a working arm part 121 having a lever shaft 121a, which is rotatably coupled to the rear end portion of the cylinder housing 110, formed at one end portion and a handle part 122 extending from the other end portion of the working arm part 121 by being bent at a slight angle. As illustrated in FIG. 2A, the handle part 122 is configured to be rotatable to a folded position where the handle part 122 entirely lies on the cylinder housing 110. FIG. 2B illustrates a position where the loading lever 120 is completely opened.

One end portion of a link 140, which is at a position spaced apart from the lever shaft 121a of the working arm part 121, is coupled to the lever shaft 121a of the working arm part 121 via a hinge pin 121b. The other end portion of the link 140 extends to the inside of the cylinder housing 110 and is coupled to a towing member 130 via a hinge pin 140a. Accordingly, the towing member 130 slides forward or backward inside the cylinder housing 110 due to the link 140 according to the rotation of the loading lever 120.

An inner cylinder 150 configured to be coupled to a front portion of the towing member 130 is provided inside the cylinder housing 110. A spring 160 is inserted inside the inner cylinder 150, and an actuating head 170 is inserted into a front portion of the spring 160. A front end portion of the inner cylinder 150 is coupled to a stopper 151, which has a passage 151a formed at a central portion, and is closed thereby.

According to the above-described configuration, when the loading lever 120 is rotated from the folded position illustrated in FIG. 2A to the position illustrated in FIG. 2B, the inner cylinder 150 inside the cylinder housing 110 is pulled rearward.

Here, the inner cylinder 150 has a slit 152 extending rearward from the front end portion, and, corresponding to the slit 152, the actuating head 170 has a catching protrusion 171 disposed at one side and configured to be inserted into the slit 152. Also, the trigger lever 180, which is coupled to the outer side of the cylinder housing 110, has a stopper head part 182 formed at one side with respect to a hinge shaft 181, which is rotatably coupled to the outer side of the cylinder housing 110, so as to be able to pass through the cylinder housing 110 and be inserted into the slit 152 of the inner cylinder 150.

Figure 3A:
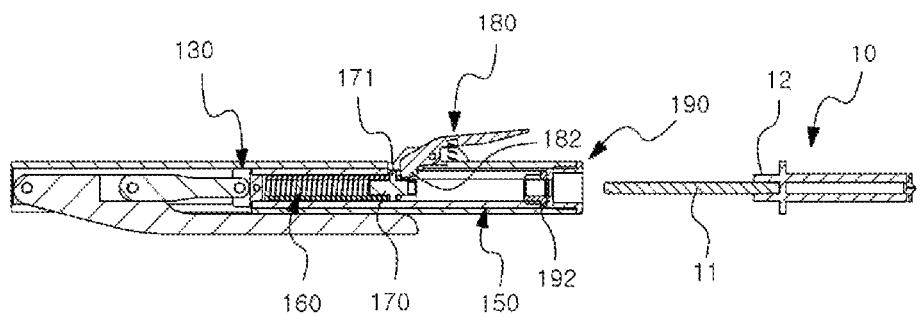
FIG. 3A is a cross-sectional view illustrating a process of using the needleless injector of FIG. 1 step by step.

According to the above-described configuration, at the position illustrated in FIG. 2B where the inner cylinder 150 is pulled rearward, the actuating head 170 of the inner side, which moves rearward together with the inner cylinder 150, passes rearward while pushing the stopper head part 182 so that the stopper head part 182 rotates outward (or pressing a pressing part 183 of the trigger lever 180 so as not to get caught on the stopper head part 182 thereof). Then, when returning the loading lever 120 to the folded position illustrated in FIG. 2A, as illustrated in FIG. 3A, the catching protrusion 171 of the actuating head 170 is caught on the stopper head part 182 of the trigger lever 180, and the actuating head 170 stops. Therefore, the actuating head 170 reaches a loaded state due to the spring 160 which is compressed between the towing member 130 and the actuating head 170.

Figure 3B:
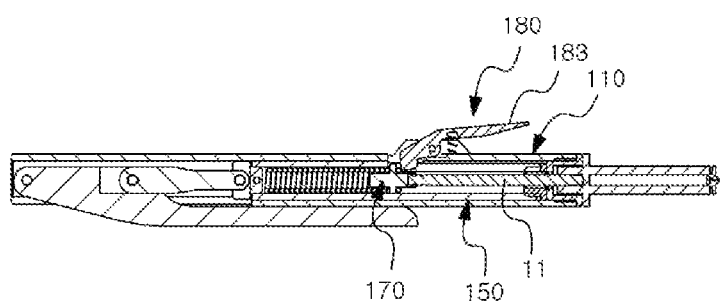
FIG. 3B is a cross-sectional view illustrating a process of using the needleless injector of FIG. 1 step by step.
Figure 3C:
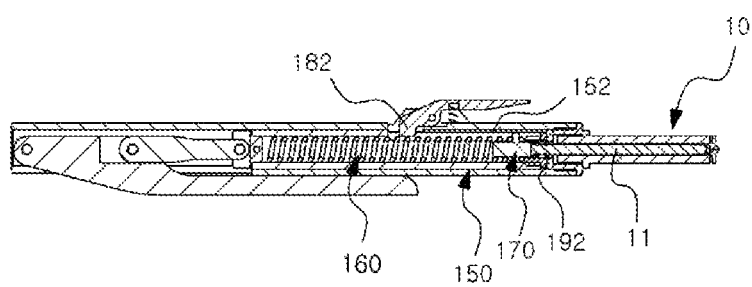
FIG. 3C is a cross-sectional view illustrating a process of using the needleless injector of FIG. 1 step by step.
Figure 3D:
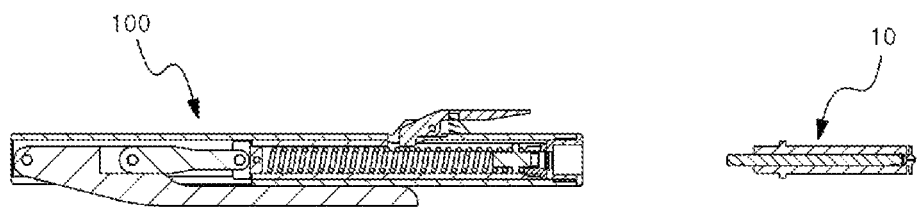
FIG. 3D is a cross-sectional view illustrating a process of using the needleless injector of FIG. 1 step by step.

When an injection solution nozzle 10 is mounted in the state in which the actuating head 170 is loaded as illustrated in FIG. 3A, as illustrated in FIG. 3B, a nozzle-side piston rod 11 is inserted from the front end portion of the cylinder housing 110, passes through the front end portion of the inner cylinder 150, and comes in contact with the actuating head 170 loaded as described above. In this state, when the pressing part 183 of the trigger lever 180 is pressed, as illustrated in FIG. 3C, the stopper head part 182 is detached outward from the slit 152 of the inner cylinder 150, and, simultaneously, the actuating head 170 is pushed forward due to a force of the compressed spring 160 attempting to expand. Thus, the piston rod 11 is pushed and the injection solution in the nozzle 10 is discharged forward. As illustrated in FIG. 3D, the nozzle 10 from which the injection solution is discharged is separated from the needleless injector 100.

Referring to FIG. 2, as the cylinder housing 110 has a cut section 111 extending forward from the rear end portion to which the lever shaft 121a is coupled, movements of the working arm part 121 and the link 140 according to the rotation of the loading lever 120 occur through the cut section 111, and, in implementation of the operation mechanism, conflict does not occur between components. Further, as illustrated in FIG. 2A, at the folded position of the handle part 122, an upper end portion of the working arm part 121 is accommodated in the cylinder housing 110 through the cut section 111, and the link 140 is completely accommodated in the cylinder housing 110 through the cut section 111. In this way, the thickness of the needleless injector 100 may be further reduced while the loading lever 120 is included in the needleless injector 100.

The needleless injector 100 includes a plug 190 coupled to the front end portion of the cylinder housing 110. In the plug 190, a seating space is formed on an inner circumferential surface of a cylindrical part 191, whose outer circumferential surface is screw-coupled to an inner circumferential surface of the front end portion of the cylinder housing 110, so that a proximal end portion 12 (see FIG. 3) at the nozzle 10 side is inserted and seated on the seating space, and a through-hole 192a is formed in a central portion of a blocking plate part 192, which extends radially inward from a rear end portion of the cylindrical part 191, so that the piston rod 11 may pass through the through-hole 192a. The blocking plate part 192 supports the front end portion of the inner cylinder 150 in the state in which the actuating head 170 is loaded as illustrated in FIG. 3A. The blocking plate part 192 supports the front end portion of the inner cylinder 150 even when the actuating head 170 is triggered as illustrated in FIG. 3C, thereby serving to absorb impact.

Figure 4:
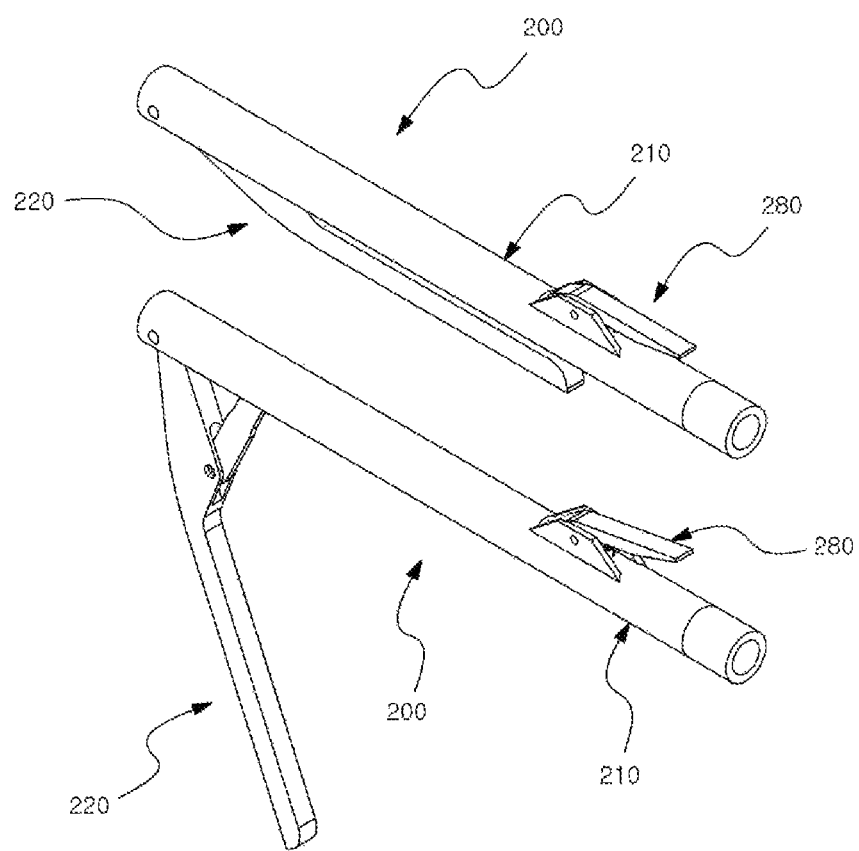
FIG. 4 is a perspective view illustrating states before and after the operation of a needleless injector according to a second embodiment of the present invention.

As illustrated in FIG. 4, a needleless injector 200 according to a second embodiment of the present invention includes a cylinder housing 210, a loading lever 220 rotatably coupled to a rear end portion of the cylinder housing 210, and a trigger lever 280 coupled to an outer side of the cylinder housing 210.

Figure 5A:
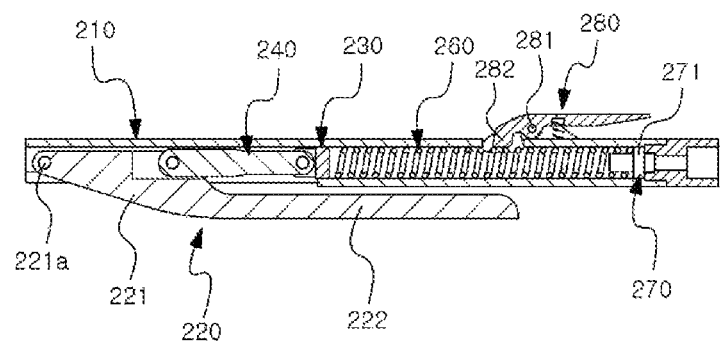
FIG. 5A is a cross-sectional view of the state before the operation of the needleless injector of FIG. 4.
Figure 5B:
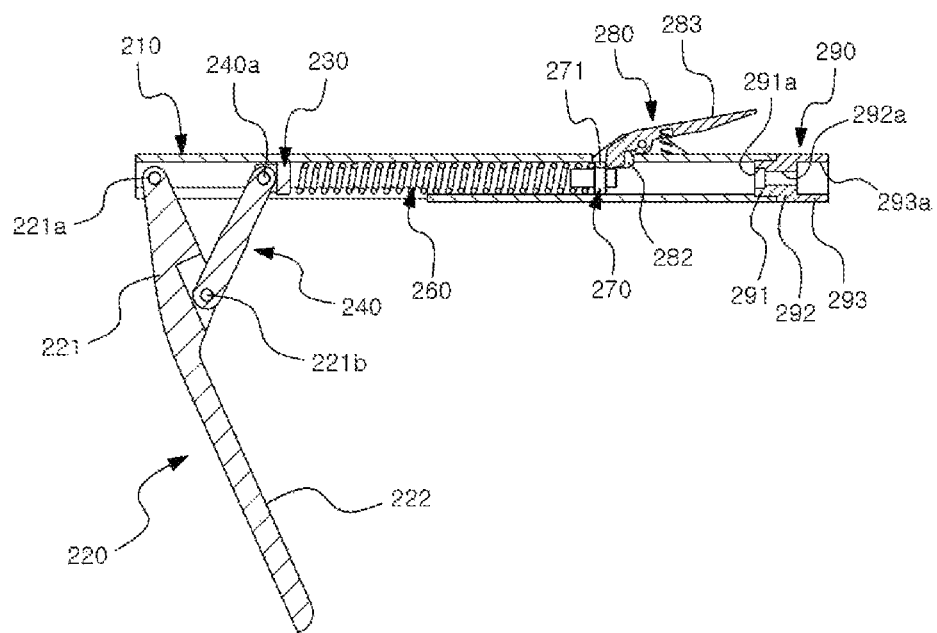
FIG. 5B is a cross-sectional view of the state after the operation of the needleless injector of FIG. 4.

As illustrated in FIG. 5, the loading lever 220 has a working arm part 221 having a lever shaft 221a, which is rotatably coupled to the rear end portion of the cylinder housing 210, formed at one end portion and a handle part 222 extending from the other end portion of the working arm part 221 by being bent at a slight angle. As illustrated in FIG. 5A, the handle part 222 is configured to be rotatable to a folded position where the handle part 222 entirely lies on the cylinder housing 210. FIG. 5B illustrates a position where the loading lever 220 is completely opened.

One end portion of a link 240, which is at a position spaced apart from the lever shaft 221a of the working arm part 221, is coupled to the lever shaft 221a of the working arm part 221 via a hinge pin 221b. The other end portion of the link 240 extends to the inside of the cylinder housing 210 and is coupled to a towing member 230 via a hinge pin 240a. Accordingly, the towing member 230 slides forward or backward inside the cylinder housing 210 due to the link 240 according to the rotation of the loading lever 220.

A spring 260 configured to be coupled to a front portion of the towing member 230 is provided inside the cylinder housing 210, and an actuating head 270 is coupled to a front portion of the spring 260. The coupling between the spring 260 and the actuating head 270 may be performed using methods such as welding, mechanical coupling, and bonding.

According to the above-described configuration, when the loading lever 220 is rotated from the folded position illustrated in FIG. 5A to the position illustrated in FIG. 5B, the towing member 230, the spring 260, and the actuating head 270 which are inside the cylinder housing 210 are pulled rearward.

Here, the actuating head 270 has a catching protrusion 271 configured to protrude radially toward an inner circumferential surface of the cylinder housing 210, and the trigger lever 280, which is coupled to the outer side of the cylinder housing 210, has a stopper head part 282 formed at one side with respect to a hinge shaft 281, which is rotatably coupled to the outer side of the cylinder housing 210, so as to be able to pass through the cylinder housing 210 and protrude inward.

Figure 6A:
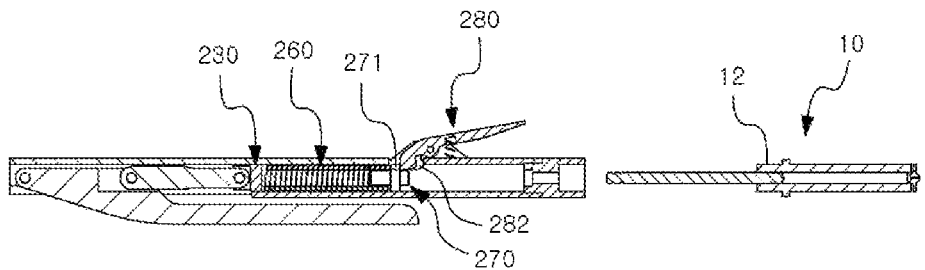
FIG. 6A is a cross-sectional view illustrating a process of using the needleless injector of FIG. 4 step by step.

According to the above-described configuration, at the position illustrated in FIG. 5B where the towing member 230, the spring 260, and the actuating head 270 are pulled rearward, the actuating head 270 passes rearward while pushing the stopper head part 282 so that the stopper head part 282 rotates outward (or pressing a pressing part 283 of the trigger lever 280 so as not to get caught on the stopper head part 282 thereof). Then, when returning the loading lever 220 to the folded position illustrated in FIG. 5A, as illustrated in FIG. 6A, the catching protrusion 271 of the actuating head 270 is caught on the stopper head part 282 of the trigger lever 280, and the actuating head 270 stops. Therefore, the actuating head 270 reaches a loaded state due to the spring 260 which is compressed between the towing member 230 and the actuating head 270.

Figure 6B:
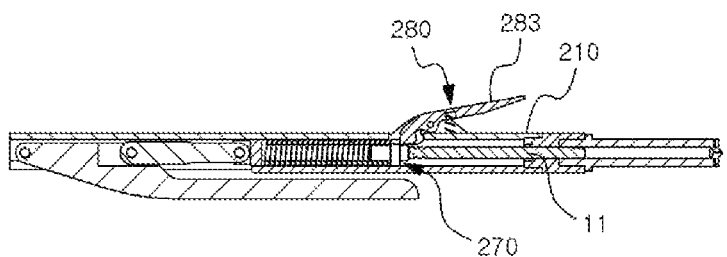
FIG. 6B is a cross-sectional view illustrating a process of using the needleless injector of FIG. 4 step by step.
Figure 6C:
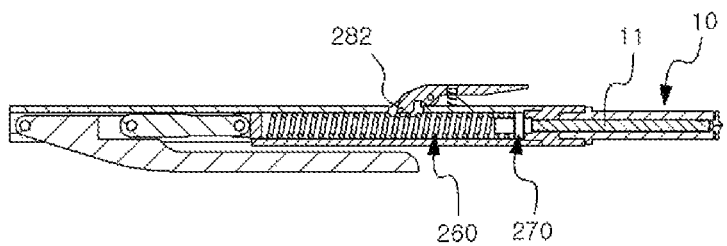
FIG. 6C is a cross-sectional view illustrating a process of using the needleless injector of FIG. 4 step by step.
Figure 6D:
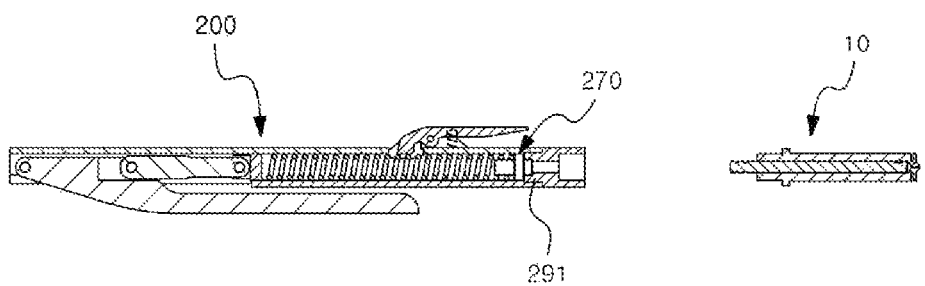
FIG. 6D is a cross-sectional view illustrating a process of using the needleless injector of FIG. 4 step by step.

When an injection solution nozzle 10 is mounted in the state in which the actuating head 270 is loaded as illustrated in FIG. 6A, as illustrated in FIG. 6B, a nozzle-side piston rod 11 is inserted from the front end portion of the cylinder housing 210 and comes in contact with the actuating head 270 loaded as described above. In this state, when the pressing part 283 of the trigger lever 280 is pressed, as illustrated in FIG. 6C, the stopper head part 282 is detached outward, and, simultaneously, the actuating head 270 is pushed forward due to a force of the compressed spring 260 attempting to expand. Thus, the piston rod 11 is pushed, and the injection solution in the nozzle 10 is discharged forward. As illustrated in FIG. 6D, the nozzle 10 from which the injection solution is discharged is separated from the needleless injector 200.

Referring to FIG. 5, the needleless injector 200 includes a plug 290 coupled to the front end portion of the cylinder housing 210. The plug 290 is screw-coupled to an inner circumferential surface of the front end portion of the cylinder housing 210 and is provided to accommodate the actuating head 270 through an accommodating groove 291a formed in a blocking wall part 291, which is formed at a rear end portion of the plug 290. A through-hole 292a communicating with the accommodating groove 291a is formed to extend in a central portion of a passage part 292, which is formed at a middle portion of the plug 290. A seating space 293a communicating with the through-hole 292a is formed in a cylindrical part 293, which is formed at a front end portion of the plug 290.

The blocking wall part 291 accommodates and supports the actuating head 270 when the actuating head 270 is triggered as illustrated in FIG. 6C, thereby serving to absorb impact. The nozzle-side piston rod 11 may pass through the through-hole 292a of the passage part 292. A proximal end portion 12 (see FIG. 6) at the nozzle 10 side may be inserted and seated on the seating space 293a on an inner circumferential surface of the cylindrical part 293.

Figure 7:
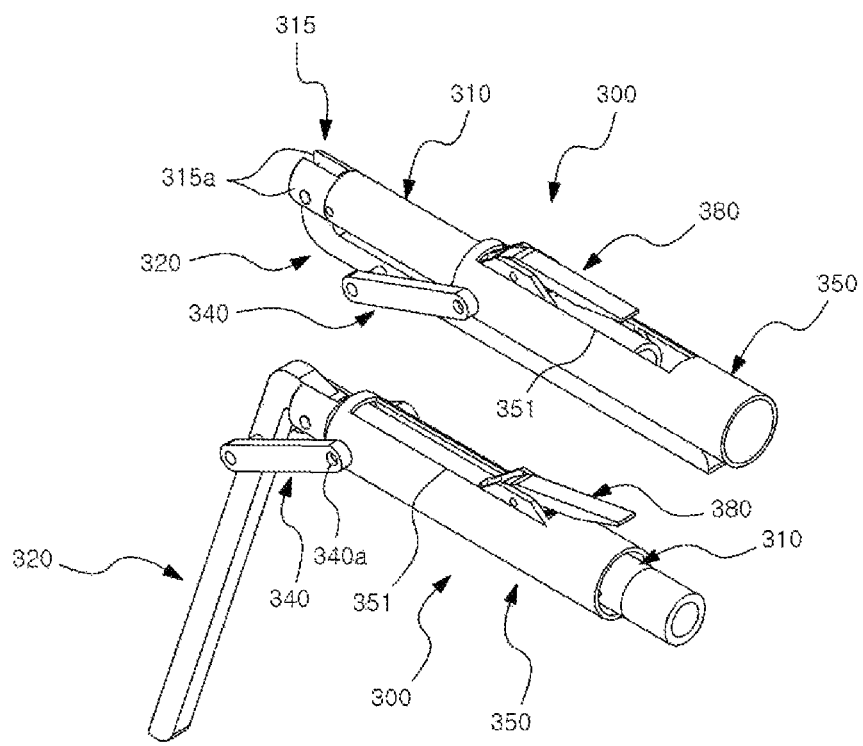
FIG. 7 is a perspective view illustrating states before and after the operation of a needleless injector according to a third embodiment of the present invention.

As illustrated in FIG. 7, a needleless injector 300 according to a third embodiment of the present invention includes a cylinder housing 310, a loading lever 320 rotatably coupled to a rear end portion of the cylinder housing 310, a loading cylinder 350 coupled to an outer side of the cylinder housing 310 so as to be able to slide back and forth, and a trigger lever 380 coupled to the outer side of the cylinder housing 310 through an open section 351 of the loading cylinder 350.

Figure 8A:
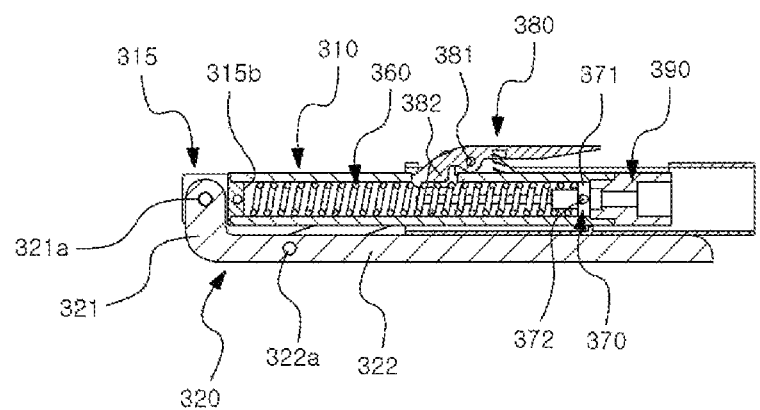
FIG. 8A is a cross-sectional view of the states before the operation of the needleless injector of FIG. 7.
Figure 8B:
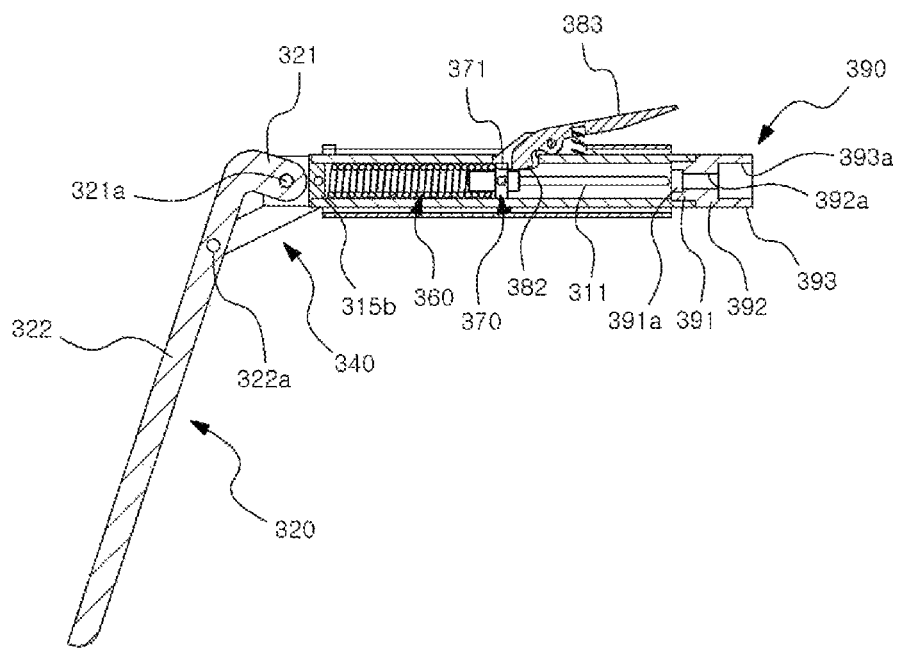
FIG. 8B is a cross-sectional view of the states after the operation of the needleless injector of FIG. 7.

As illustrated in FIGS. 7 and 8, the loading lever 320 has a working arm part 321 having a lever shaft 321a, which is rotatably coupled to a shaft accommodating part 315a provided in a hinge plug 315 coupled to the rear end portion of the cylinder housing 310, formed at one end portion and a handle part 322 extending from the other end portion of the working arm part 321 by being bent at a right angle. As illustrated in FIG. 8A, the handle part 322 is configured to be rotatable to a folded position where the handle part 322 entirely lies on the cylinder housing 310. FIG. 8B illustrates a position where the loading lever 320 is completely opened. The hinge plug 315 forms a stopper wall 315b by being coupled to the rear end portion of the cylinder housing 310.

One end portion of a link 340, which is at a position adjacent to the lever shaft 321a of the working arm part 321, is coupled to the handle part 322 via a hinge pin 322a. The other end portion of the link 340 is coupled to a rear end portion of the loading cylinder 350 via a hinge pin 340a. Accordingly, the loading cylinder 350 slides forward or backward outside the cylinder housing 310 due to the link 340 according to the rotation of the loading lever 320.

A spring 360 is inserted inside the cylinder housing 310, and an actuating head 370 is inserted into a front portion of the spring 360. As will be described below, a plug 390 is coupled to the front end portion of the cylinder housing 310. A loading protrusion 372 is formed at both left and right side surfaces of the actuating head 370. The loading protrusions 372 pass through a slit 311, which is formed to extend rearward from the front end portion of the cylinder housing 310, and are coupled to an inner circumferential surface of the loading cylinder 350.

According to the above-described configuration, when the loading lever 320 is rotated from the folded position illustrated in FIG. 8A to the position illustrated in FIG. 8B, the loading cylinder 350 (see FIG. 7) at the outer side slides rearward, and, as a result, the actuating head 370 inside the cylinder housing 310 is pulled rearward.

Here, the actuating head 370 has a catching protrusion 371 configured to protrude radially toward an inner circumferential surface of the cylinder housing 310, and the trigger lever 380, which is coupled to the outer side of the cylinder housing 310, has a stopper head part 382 formed at one side with respect to a hinge shaft 381, which is rotatably coupled to the outer side of the cylinder housing 310, so as to be able to pass through the cylinder housing 310 and protrude inward.

Figure 9A:
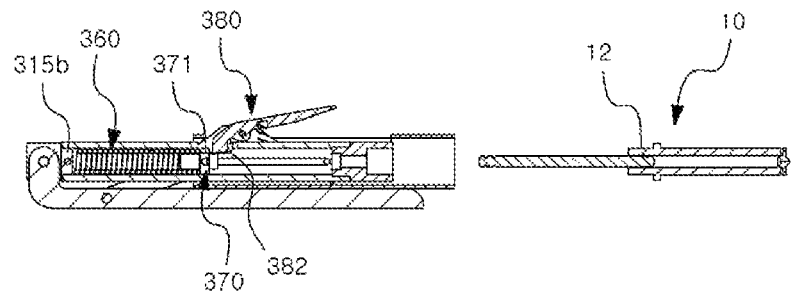
FIG. 9A is a cross-sectional view illustrating a process of using the needleless injector of FIG. 7 step by step.

According to the above-described configuration, at the position illustrated in FIG. 8B where the loading cylinder 350 is pulled rearward, the actuating head 370 of the inner side, which moves rearward together with the loading cylinder 350, passes rearward while pushing the stopper head part 382 so that the stopper head part 382 rotates outward (or pressing a pressing part 383 of the trigger lever 380 so as not to get caught on the stopper head part 382 thereof). Then, when returning the loading lever 320 to the folded position illustrated in FIG. 8A, as illustrated in FIG. 9A, the catching protrusion 371 of the actuating head 370 is caught on the stopper head part 382 of the trigger lever 380, and the actuating head 370 stops. Therefore, the actuating head 370 reaches a loaded state due to the spring 360 which is compressed between the stopper wall 315b and the actuating head 370.

Figure 9B:
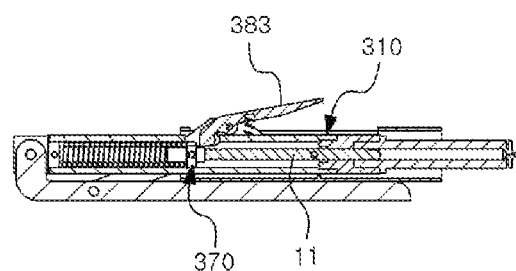
FIG. 9B is a cross-sectional view illustrating a process of using the needleless injector of FIG. 7 step by step.
Figure 9C:
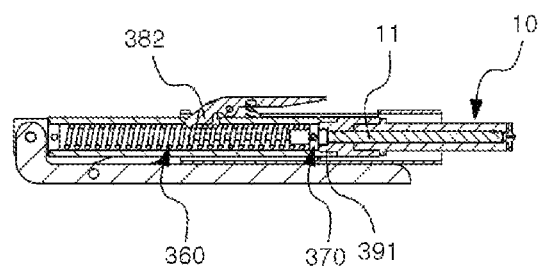
FIG. 9C is a cross-sectional view illustrating a process of using the needleless injector of FIG. 7 step by step.
Figure 9D:
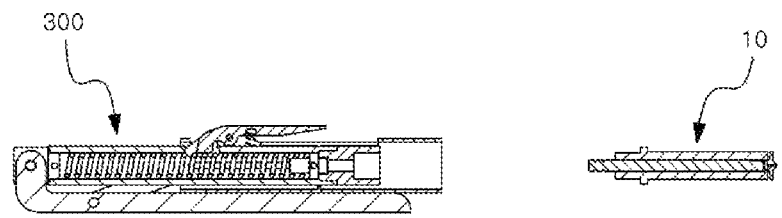
FIG. 9D is a cross-sectional view illustrating a process of using the needleless injector of FIG. 7 step by step.

When an injection solution nozzle 10 is mounted in the state in which the actuating head 370 is loaded as illustrated in FIG. 9A, as illustrated in FIG. 9B, a nozzle-side piston rod 11 is inserted from the front end portion of the cylinder housing 310 and comes in contact with the actuating head 370 loaded as described above. In this state, when the pressing part 383 of the trigger lever 380 is pressed, as illustrated in FIG. 9C, the stopper head part 382 is detached outward, and, simultaneously, the actuating head 370 is pushed forward due to a force of the compressed spring 360 attempting to expand. Thus, the piston rod 11 is pushed and the injection solution in the nozzle 10 is discharged forward. As illustrated in FIG. 9D, the nozzle 10 from which the injection solution is discharged is separated from the needleless injector 300.

Referring to FIG. 8, the needleless injector 300 includes the plug 390 coupled to the front end portion of the cylinder housing 310. The plug 390 is screw-coupled to an inner circumferential surface of the front end portion of the cylinder housing 310 and is provided to accommodate the actuating head 370 through an accommodating groove 391a formed in a blocking wall part 391, which is formed at a rear end portion of the plug 390. A through-hole 392a communicating with the accommodating groove 391a is formed to extend in a central portion of a passage part 392, which is formed at a middle portion of the plug 390. A seating space 393a communicating with the through-hole 392a is formed in a cylindrical part 393, which is formed at a front end portion of the plug 390.

The blocking wall part 391 accommodates and supports the actuating head 370 when the actuating head 370 is triggered as illustrated in FIG. 9C, thereby serving to absorb impact. The nozzle-side piston rod 11 may pass through the through-hole 392a of the passage part 392. A proximal end portion 12 (see FIG. 9) at the nozzle 10 side may be inserted and seated on the seating space 393a on an inner circumferential surface of the cylindrical part 393.

The needleless injector according to the present invention can achieve a reduction in size and thickness by having a simple structure even with a lever for reloading integrally formed therein.

The needleless injectors 100, 200, and 300 which have been described above are merely embodiments for assisting the understanding of the present invention, and thus the scope or technical scope of the present invention should not be understood as being limited by the above descriptions. The scope or technical scope of the present invention is defined by the appended claims and their equivalents.

What is claimed is:

1. A needleless injector comprising:
   a cylinder housing;
   a loading lever having a working arm part having a lever shaft, which is rotatably coupled to a rear end portion of the cylinder housing, formed at one end portion and a handle part extending from the other end portion of the working arm part by being bent at a predetermined angle so that the handle part is rotatable to a folded position where the handle part lies on the cylinder housing;
   a towing member inserted inside the cylinder housing;
   a link having one end portion spaced apart from the lever shaft and pin-coupled to the working arm part and the other end portion pin-coupled to the towing member so that the towing member is able to slide back and forth inside the cylinder housing according to a rotation of the loading lever;
   an inner cylinder inserted inside the cylinder housing so as to be able to slide back and forth and having a rear end portion integrally coupled to the towing member, a front end portion configured to be closed by a stopper having a passage formed therein, and a slit extending rearward from the front end portion;
   a spring inserted inside the inner cylinder;
   an actuating head inserted inside the inner cylinder so as to be able to slide back and forth in front of the spring and having a catching protrusion configured to be inserted into the slit; and
   a trigger means coupled to an outer side of the cylinder housing and having a stopper head part configured to pass through the cylinder housing so as to be able to be inserted into the slit of the inner cylinder and detached from the slit,
   wherein the cylinder housing has a cut section extending forward from the rear end portion to which the lever shaft is coupled,
   movements of the working arm part and the link according to the rotation of the loading lever occur through the cut section, and
   at the folded position of the handle part, the working arm part is at least partially accommodated in the cylinder housing through the cut section, and the link is completely accommodated in the cylinder housing through the cut section.

2. The needleless injector of claim 1, wherein the trigger means includes a trigger lever having the stopper head part formed at one side and a pressing part, which is configured to detach the stopper head part from the slit, formed at the other side with respect to a hinge shaft rotatably coupled to the outer side of the cylinder housing.

3. The needleless injector of claim 1, further comprising a plug having a cylindrical part, whose outer circumferential surface is screw-coupled to an inner circumferential surface of a front end portion of the cylinder housing and whose inner circumferential surface forms a seating space, and a blocking plate part extending radially inward from a rear end portion of the cylindrical part and having a through-hole formed at a central portion.

4. A needleless injector comprising:
   a cylinder housing;
   a loading lever having a working arm part having a lever shaft, which is rotatably coupled to a rear end portion of the cylinder housing, formed at one end portion and a handle part extending from the other end portion of the working arm part by being bent at a predetermined angle so that the handle part is rotatable to a folded position where the handle part lies on the cylinder housing;

a towing member inserted inside the cylinder housing;

a link having one end portion spaced apart from the lever shaft and pin-coupled to the working arm part and the other end portion pin-coupled to the towing member so that the towing member is able to slide back and forth inside the cylinder housing according to a rotation of the loading lever;

a spring inserted inside the cylinder housing and whose rear end portion is coupled to the towing member;

an actuating head inserted inside the cylinder housing, coupled to a front end portion of the spring, and having a catching protrusion configured to protrude radially toward an inner circumferential surface of the cylinder housing; and a trigger means coupled to an outer side of the cylinder housing and having a stopper head part configured to pass through the cylinder housing so as to be able to protrude and be detached from the inside of the cylinder housing, wherein the cylinder housing has a cut section extending forward from the rear end portion to which the lever shaft is coupled, movements of the working arm part and the link according to the rotation of the loading lever occur through the cut section, and at the folded position of the handle part, the working arm part is at least partially accommodated in the cylinder housing through the cut section, and the link is completely accommodated in the cylinder housing through the cut section.

5. The needleless injector of claim 4, wherein the trigger means includes a trigger lever having the stopper head part formed at one side and a pressing part, which is configured to detach the stopper head part from the inside of the cylinder housing, formed at the other side with respect to a hinge shaft rotatably coupled to the outer side of the cylinder housing.

6. The needleless injector of claim 4, further comprising a plug screw-coupled to a front end portion of the cylinder housing and having, from a rear end portion thereof, a blocking wall part, which has an accommodating groove formed to accommodate the actuating head, a passage part, which has a through-hole communicating with the accommodating groove formed to extend at a central portion, and a cylindrical part, which has an inner circumferential surface on which an inner seating space communicating with the through-hole is formed, sequentially formed in this order.

7. A needleless injector comprising:

a cylinder housing having a stopper wall formed at a rear end portion and a slit extending rearward from a front end portion;

a loading lever having a working arm part having a lever shaft, which is rotatably coupled to the cylinder housing behind the stopper wall, formed at one end portion and a handle part extending from the other end portion of the working arm part by being bent at a predetermined angle so that the handle part is rotatable to a folded position where the handle part lies on the cylinder housing;

a spring inserted inside the cylinder housing;

an actuating head inserted inside an inner cylinder so as to be able to slide back and forth in front of the spring and having a catching protrusion, which is configured to protrude radially toward an inner circumferential surface of the cylinder housing, and a loading protrusion, which is configured to pass through the slit;

a loading cylinder configured to be coupled to an outer side of the cylinder housing so as to be able to slide back and forth, configured to be coupled to the loading protrusion of the actuating head through an inner circumferential surface, and having an open section extending in a front-rear, longitudinal direction;

a link having one end portion pin-coupled to the handle part at a position adjacent to the lever shaft and the other end portion pin-coupled to a rear end portion of the loading cylinder so that the loading cylinder is able to slide back and forth at the outer side of the cylinder housing according to a rotation of the loading lever; and a trigger means coupled to the outer side of the cylinder housing through the open section of the loading cylinder and having a stopper head part configured to pass through the cylinder housing so as to be able to protrude and be detached from the inside of the cylinder housing, wherein the cylinder housing includes a hinge plug coupled to a rear end portion of the cylinder housing and having a shaft accommodating part, to which the lever shaft is coupled, and the stopper wall.

8. The needleless injector of claim 7, wherein the working arm part and the handle part of the loading lever are perpendicular to each other.

9. The needleless injector of claim 7, wherein the trigger means includes a trigger lever having the stopper head part formed at one side and a pressing part, which is configured to detach the stopper head part from the inside of the cylinder housing, formed at the other side with respect to a hinge shaft rotatably coupled to the outer side of the cylinder housing.

10. The needleless injector of claim 7, further comprising a plug screw-coupled to a front end portion of the cylinder housing and having, from a rear end portion thereof, a blocking wall part, which has an accommodating groove formed to accommodate the actuating head, a passage part, which has a through-hole communicating with the accommodating groove formed to extend at a central portion, and a cylindrical part, which has an inner circumferential surface on which an inner seating space communicating with the through-hole is formed, sequentially formed in this order.

* * * * *